US006433162B1

United States Patent
Nickel et al.

(10) Patent No.: US 6,433,162 B1
(45) Date of Patent: Aug. 13, 2002

(54) METHOD FOR SYNTHESIZING PORPHYRIN COMPOUNDS

(75) Inventors: Eric G. Nickel; Lanny S. Liebeskind, both of Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 09/518,863

(22) Filed: Mar. 3, 2000

Related U.S. Application Data
(60) Provisional application No. 60/123,058, filed on Mar. 5, 1999.

(51) Int. Cl.$^7$ ............................................. C07D 487/08
(52) U.S. Cl. ....................................... 540/145
(58) Field of Search ......................................... 540/145

(56) References Cited

U.S. PATENT DOCUMENTS

| | | | |
|---|---|---|---|
| 3,579,533 A | 5/1971 | Yalman et al. | 260/314 |
| 5,241,062 A | 8/1993 | Wijesekera et al. | 540/145 |
| 5,284,647 A | 2/1994 | Niedballa et al. | 424/81 |
| 5,284,831 A | 2/1994 | Kahl et al. | 514/21 |
| 5,659,029 A | 8/1997 | Ellis, Jr. et al. | 540/145 |
| 5,672,717 A | 9/1997 | Verkade et al. | 548/518 |
| 5,674,467 A | 10/1997 | Maier et al. | 424/1.65 |
| 5,703,230 A | 12/1997 | Boyle et al. | 540/145 |

FOREIGN PATENT DOCUMENTS

| | | | |
|---|---|---|---|
| JP | 63238078 | | 4/1988 |
| JP | 63238057 | | 10/1988 |
| JP | 1238585 | | 9/1989 |
| SU | 1553060 | | 3/1990 |
| WO | WO 00/56706 | * | 9/2000 |

OTHER PUBLICATIONS

Fujii et al., Chemical Abstracts, vol. 126:263974, 1997.*
Triebs et al., Chemical Abstracts, vol. 76:3820, 1972.*
Rodd's Chemistry of Carbon Compounds, 2$^{nd}$ Ed., vol. IV, Part B, "Heterocyclic Compounds", pp. 262–267, Elsevier, 1977.
Houben–Weyl, "Methods of Organic Chemistry", 4$^{th}$ Ed., vol. E 9d, "Hetarenes IV", pp. 596–597; George Thieme Verlag 1998.
Barton, et al. "Comprehensive Organic Chemistry. The Synthesis and Reactions of Organic Compounds" vol. 4, pp. 333–339, Pergamon Press 1979.
Kadish et al. Inorg. Chem. 24 (1985) 4512.*
Ogose et al,. Chemical Abstracts 111:39183 (abstract for JP63238057) 1989.*
Buchler in The Porphyrins, vol. 1 Structure and Synthesis, Part A, ed. D. Dolphin, Academic Press, New York, 1978, pp. 389–482.*
Anderson, et al., *The Synthesis of 3–Substituted Pyrroles from Pyrrole;* Synthesis 353–364 (1985).
Mueller–Westerhoff, et al., *Azines and Imines of 4– and 5–t–Bu–Pyrrole–2–Aldehyde, A Useful Synthesis of the Aldehydes;*Synthetic Communications 24(10) 1389–1393 (1994).
Kuroda, et al., *A New Route For Meso–Substituted Porphyrin;* Tertahedron Letters, vol. 30, No. 18, pp. 2411–2412, (1989).
Longo, et al., *Notes on the Synthesis of Porphin;* J. Heterocyclic Chem. 12, 1305–1309 (1975).
Ono, et al., *A Convenient Synthesis of Trifluoromethylated Pyrroles and Porphyrins;* Bulletin of the Chemical Society of Japan; vol. 62, No. 10 3386–3388 (1989).
Ono, et al., *A New Synthesis of Porphyrins via Tetramerization of 2–(Hydroxymethyl) pyrroles:* The Chemical Society of Japan, Chemistry Letters vol. 7, pp. 1237–1240 (1989).
Kinoshita, et al., *Synthesis of 2–(Substituted Methyl)–3, 4–Disubstituted Pyrroles and Their Conversion into the Corresponding Porphyrins;* Bull. Chem Soc. Jpn. 65, 2660–2667 (1992).
Whitlock, et al., *Cyclotetramerization of 2–Dimethylamino–4–6tert–butylpyrrole; The Tetra–tert–butylporphyrins:* J. Amer. Chem. Soc. 96, 3955–3965 (1974).
Ellis, Jr. et al., *Novel Biphasic Synthesis of Porphyrin;* J. Porphyrins Phthalocynines 1, 305–307 (1997).
Anderson et al. Pyrrole Chemistry V. Friedel–Crafts Isopropylations of Some Pyrrole Derivatives, Can. J. Chem. 44 1831–1839 (1966).

* cited by examiner

Primary Examiner—Richard L. Raymond
(74) Attorney, Agent, or Firm—Needle & Rosenberg, P.C.

(57) ABSTRACT

A method for synthesizing porphyrin compounds includes the step of removing one or more substituent groups from a substituted porphyrin compound. Preferably, the removal step involves acid cleavage and the substituent group is an acid cleavable substituent such as a t-butyl group. Another aspect involves a method which produces porphyrin compounds from substituted pyrrole compounds, where the substituent on the pyrrole compound selected so as to aid in the porphyrin ring formation, which substituent can be subsequently removed. In this regard, the method comprises (i) reacting the substituted pyrrole compound so as to provide a substituted porphyrin compound containing the substituent(s) followed by (ii) removal of the substituents from the substituted porphyrin compound.

14 Claims, No Drawings

METHOD FOR SYNTHESIZING PORPHYRIN COMPOUNDS

CROSS REFERENCE TO RELATED APPLICATIONS

This application is related to copending provisional application Serial No. 60/123,058, filed Mar. 5, 1999, which is incorporated by reference, and claims the benefit of its earlier filing date under 35 USC Section 119(e).

BACKGROUND OF THE INVENTION

The present invention relates to porphyrin compounds, pyrrole compounds useful in making the porphyrin compounds and methods for synthesizing porphyrin compounds.

Porphyrin compounds as well as methods for synthesizing the same are well recognized in the art. However, porphyrin compounds are very expensive. For example, porphine is offered at costs as high as $15,000/g. The current best-known porphine synthesis entails the tetramerzation of hydroxymethylpyrrole, an unsubstituted pyrrole monomer. The lack of substituents requires high dilution (e.g., 0.005M porphine) to obtain optimal yields (i.e., 15%). Purification by alumina chromatography is both necessary and tedious due to the very low solubility of porphine.

Attention is directed towards the following patents and scientific publications related to porphyrins and their synthesis which are herein incorporated by reference in their entirety. U.S. Pat. No. 3,579,533 to Yalman; U.S. Pat. No. 5,241,062 to Wijesekera, et al.; U.S. Pat. No. 5,659,029 to Ellis Jr. et al.; U.S. Pat. No. 5,674,467 to Maier et al.; U.S. Pat. No. 5,703,230 to Boyle et al.; U.S. Pat. No. 5,284,831 to Kahl et al; JP 1238585 A, assigned to Maruyamaka; JP 63238078 A, assigned to Central Glass Co. Ltd.; JP 63238057 A., assigned to Central Glass Co. Ltd.; and SU 1553060 A, assigned to Ivan Mother Child; *Synthesis*, Anderson et al, (1985) 353; *Synthetic Communications*, Mueller-Westerhoff et al, 24(10), 1389–1393 (1994); *Tetrahedron Letters*, Kuroda et al., 30(18), 2411–2412 (1989); *J. Heterocyclic Chem.*, Longo et al., 12,1305–1309 (1975); *Bull. Chem. Soc. Jpn.*, Ono et al., 62, 3386–3388 (1989); *Chem. Lett.*, Ono et al., 1237–1240 (1989); *Bull. Chem. Soc. Jpn.*, Kinoshita et al., 65, 2660–2667 (1992); *J. Amer. Chem. Soc.*, Whitlock et al., 96(12) 3959–3965 (1974); and *J Porphyrins Phthalocyanines*, Ellis et al., Vol. 1, 305–307 (1997).

Longo et al. disclose a slow and low-yield synthesis of unsubstituted porphyrin (porphin) by condensation of 2-hydroxymethyl-pyrrole in dilute solutions, at near neutral pH. As a result, porphin is unpatentable.

U.S. Pat. No. 3,579,533 to Yalman discloses a method for synthesizing porphyrins and metal chelates of porphyrins, comprising condensation of 2-hydroxylalkyl-pyrroles having primary of secondary carbinols in the pyrrole 2-position. The condensation occurs in the presence of acids and/or optional metal salts.

Ellis et al. (in the Journal of Porphyrins and Phthalocyanines) disclose synthesis of porphin, from 2-hydroxymethyl-pyrrole, in yields up to 15.3%, by use of a two-phase reaction solvent system, comprising an aqueous solution of an acid, and a water-immiscible organic solvent. U.S. Pat. No. 5,659,029 to Ellis et al. teaches the optional presence of organic substituent groups on the 3 and 4 positions of the pyrroles, and the beta positions of the porphyrin.

Kuroda et al. disclose a method for the synthesis of 2-hydroxyalkyl-pyrroles with various alkyl and aryl substituted hydroxyalkyl groups, via acylation of pyrroles, and reduction.

Ono et al., (Bull. Chem. Soc. Jpn. 62,3386 (1989), disclose a method of preparing substituted hydroxymethyl-pyrroles by reacting organic nitro and isocyanide compounds, obtaining hydroxymethyl pyrroles with two different substituents in the pyrrole 3 and 4 positions.

Japanese patent applications JP 63238057 and JP 63238078 to Central Glass Co. Ltd. relate to methods of preparing unsymmetrically di-substituted 3,4-hydroxymethyl-pyrroles, with at least one perfluoroalkyl substituent, and condensations of the pyrroles to Type I porphyrins. Japanese patent application 1238585 to Muruyama discusses a different method of preparation of unsymmetrical 3,4-hydroxymethyl-pyrroles with a variety of alkyl substituents, and their condensation to porphyrins.

U.S. Pat. No. 5,241,062 to Wijesekera et al disclose methods of making and using "leaving group" substituents bonded to the oxygen of 2-hydroxyalkyl-pyrroles. The leaving groups included various benzoates and sulfonates. Various electron withdrawing substituents were present on the pyrroles and porphyrins.

Kinoshita et al. disclose several methods for the synthesis of 3,4-unsymmetrically disubstituted, 2-hydroxymethyl-pyrroles, in which the hydroxyl group can be replaced by a variety of "leaving groups".

U.S. Pat. No. 5,674,467 to Maier et al., and U.S. Pat. No. 5,284,647 to Niedballa et al., disclose the production of porphyrins having 5-butyl substituted phenyl groups in the porphyrin meso positions, by a well-known method of condensing 4 moles of pyrrole with 4 moles of 5-butyl-substituted benzaldehydes.

U.S. Pat. No. 5,703,230 to Boyle et al. disclose a method of iodinating one meso position of various substituted porphyrins, to yield mono-iodinated porphyrins.

Despite the knowledge possessed by those skilled in the art, the need still exists for an improved technique for synthesizing porphyrin compounds.

SUMMARY OF THE INVENTION

The present invention relates to a method of producing porphyrin compounds which is capable of providing a significantly improved porphyrin yield at a reduced cost.

To this end, one aspect of the present invention relates to a method for synthesizing porphyrin compound which includes the step of removing one or more substituent groups from a substituted porphyrin compound. Preferably, the removal step involves acid cleavage and the substituent group is an acid cleavable substituent such as a t-butyl group.

Another aspect of the present invention relates to a method which produces porphyrin compounds from substituted pyrrole compounds, where the substituent on the pyrrole compound selected so as to aid in the porphyrin ring formation, which substituent can be subsequently removed. In this regard, the method comprises (i) reacting the substituted pyrrole compound so as to provide a substituted porphyrin compound containing the substituent(s) followed by (ii) removal of the substituents from the substituted porphyrin compound.

Other aspects of the invention include porphyrin compounds and, in particular, porphyrins of formula (II),

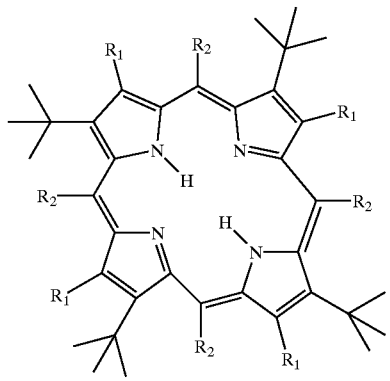

where both $R^1$ and $R^2$ are not hydrogen, and porphyrins of formula (V),

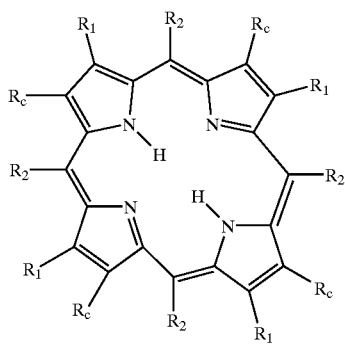

where $R_c$ is a removable substituent, e.g., an acid cleavable hydrocarbyl group such as an alkyl or aryl.

Yet additional aspects of the invention include pyrrole intermediates compounds, and, in particular, the pyrroles of formula (I), (VI) and (VII)

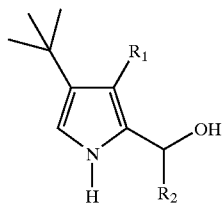

Formula I

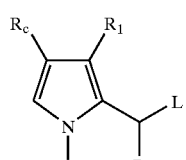

Formula VI

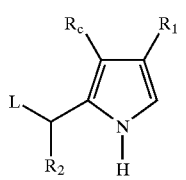

Formula VII where L is a leaving group such as a hydroxy group.

Other aspects of the presents invention include methods for synthesizing the foregoing compounds.

DETAILED DESCRIPTION OF A PREFERRED EMBODIMENT

As discussed above, the present invention relates to an improved method for synthesizing porphyrin compounds. The method includes the synthesis of porphyrin compounds from substituted porphyrin compounds where removal of the substituents provides a desired porphyrin.

In a preferred embodiment of the invention, the substituted porphyrins are themselves produced from substituted pyrrole compounds. The choice of substitutent group is largely based on two factors, (1) the ability to provide for a porphyrin ring structure during synthesis, and (2) the ability to remove and method for removing the substituent. For example, where acid cleavage is to be used in removal, the substituents preferably include tertiary carbon-containing groups such as t-butyl groups.

In particular, the removal of the substituent can be performed by cleavage reactions under acidic conditions or cleavage reactions under basic conditions. Moreover, catalytic removal processes can be performed. The preferred technique employed in the present invention relates to cleavage performed under acidic conditions. To this end, the substituent is preferably a substituent that will effectively stabilize a positive charge at that point on the porphyrin ring structure where the substituent is located. Specific examples of such suitable substituents include alkyl and aryl substituents that include tertiary carbons.

Other examples of suitable groups attached to the pyrrole-aldehyde in the 4-position via bonds other than a pyrrole-alkyl carbon bond include but not limited to aryl-R, trihalomethyl (and other halogen/methyl combinations), carbonyl-R, S—R, $B(OR)_2$, $SnR_3$, Si—$R_3$, OR, where R is a group other than hydrogen.

The substituted porphyrin compounds can include substituents in addition to the removable substituents. These additional substituents can be any substituent desired for use in connection with porphyrin compound. Examples of such substituents include hydrogen, aryl, alkyl, halogens, and the like.

One example of a synthesis method according to the present invention is illustrated by reaction scheme 1:

SCHEME I
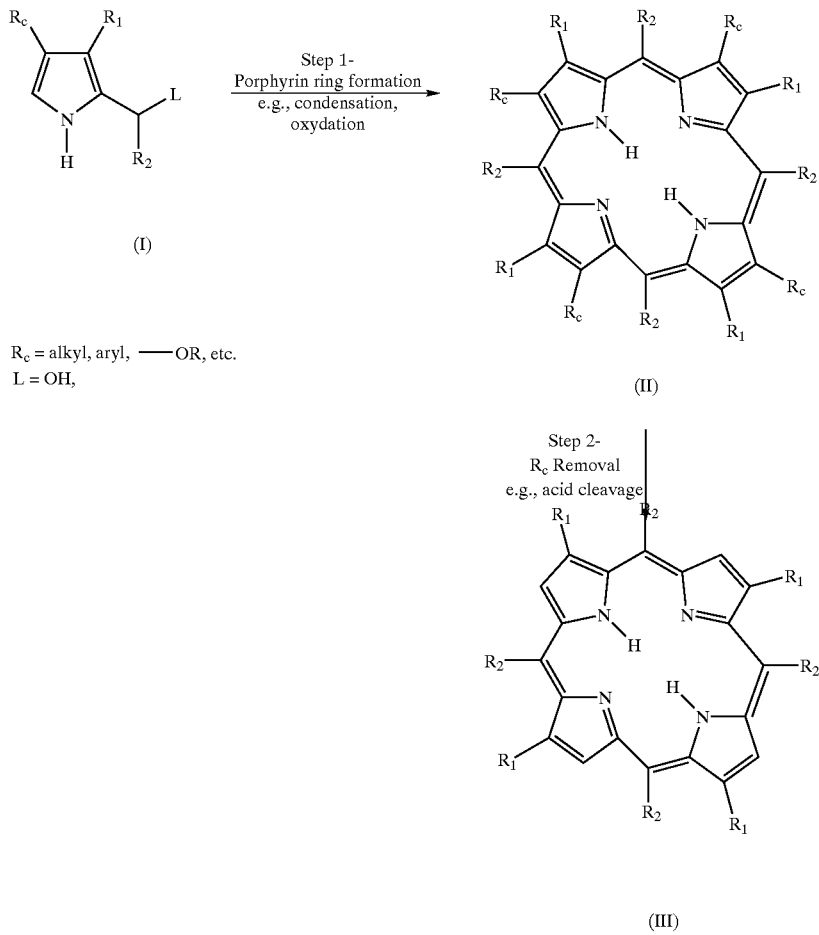
$R_c$ = alkyl, aryl, —OR, etc.
L = OH,
One specific example of this method is itself illustrated by reaction scheme 2:
SCHEME 2
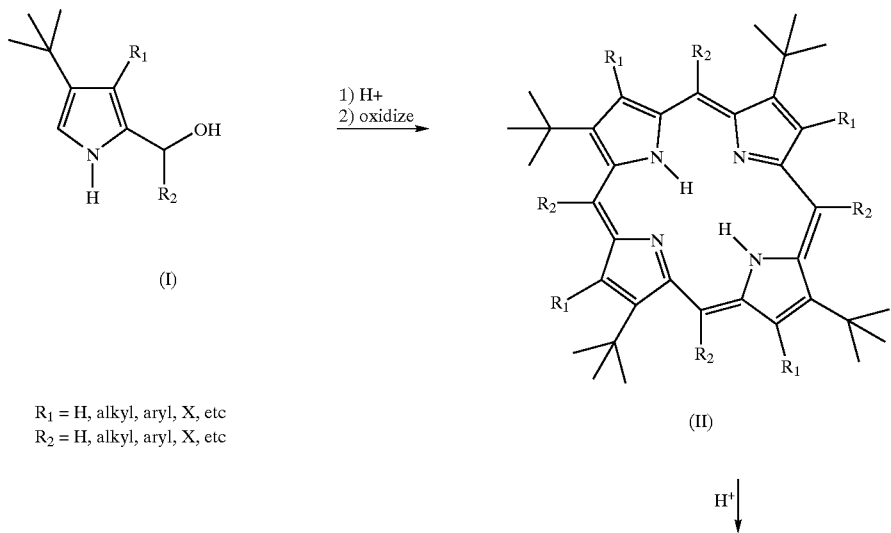
$R_1$ = H, alkyl, aryl, X, etc
$R_2$ = H, alkyl, aryl, X, etc

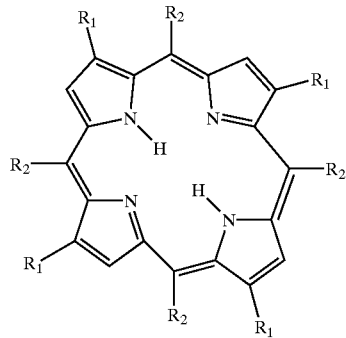

(III)

In the foregoing reaction schemes, the pyrrole compounds can be suitably reacted, e.g., condensed and oxidized, in the first "step" to provide a substituted porphyrin. Where condensation/oxidation is employed, the reaction occurs in the presence of acids such as organic acids including trifluoroacetic acid (TFA), inorganic acids such as hydrochloric acid, sulfuric acid and the like, as well as oxidants such as DDQ, chlornil and oxygen.

In on example of a suitable process, the acid is preferably introduced into a solvent such as a chlorinated solvent or an alcohol such as methanol. The pyrrole compound can then be introduced in an "effective high dilution" manner, e.g., introduced drop-wise into the acid solution.

The second "step" of the foregoing reaction schemes involves removal of the substituents from the substituted porphyrin compound. As illustrated above, this removal step can involve cleavage under acidic or basic conditions or in the optional presence of a catalyst. Preferred reaction conditions are dependent upon the exact techniques employed. In particular, where cleavage under acidic conditions are employed, the reaction is preferably employed under a combination of acid activity and temperature which is effective in removing the particular substituent involved. For example, where the substituent is a t-butyl group, one combination of suitable acid activity and temperature involves the use of $H_2SO_4 \cdot 2H_2O$ performed at reflux, i.e., about 160° C. The choice of other effective combinations of acid activity and temperature would be within the purview of those skilled in the art.

The starting materials for the foregoing synthesis method are substituted pyrrole compounds. Suitable pyrrole compounds include those of Formula (I), (VI) and (VII) which are substituted with (a) a substituent such as an acid cleavable group discussed above and (b) leaving group in this invention.

While the particular substituents associated with the term "leaving group" would be within the purview of those skilled in the art, particularly preferred substituents include —OR groups such as hydroxyl, ethers, carboxylates, benzoates, phosphates, sulfonates, sulfones and carbonyl groups. In addition, certain nitrogen based groups other than dimethylamino groups can also be employed as the leaving group.

These compounds can be produced by the following reaction scheme 3:

SCHEME 3

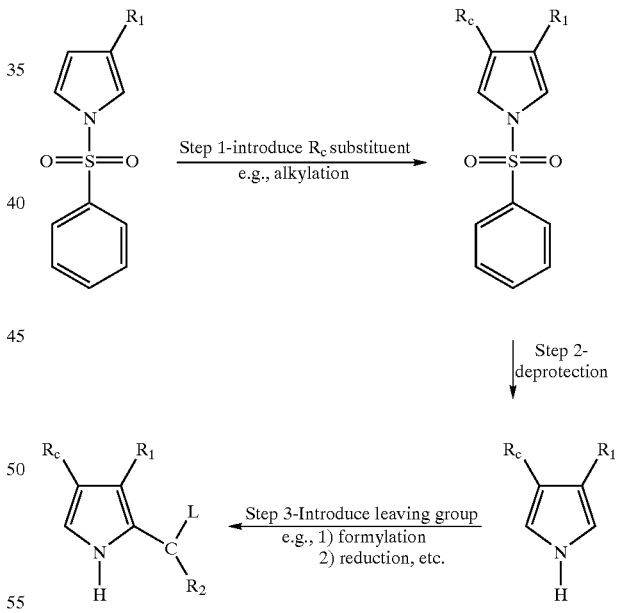

The choice of the particular synthesis step associated with each of steps 1–3 is dependant upon the particular substituents to be introduced into the molecule. For example, in connection with step 3, in addition to formylation, reduction sequence associated with hydroxy substituents, additional synthesis techniques also associated with this step can include art recognized techniques for introducing nucleophile such as $SN_2$ reactions, as well as halomethylation reactions and, in connection with nitrogen-based substituents, mannich reactions. In so far as these individual techniques are recognized in the art they need not be described in detail here. A specific example of a suitable reaction scheme 4 is as follows:

SCHEME 4

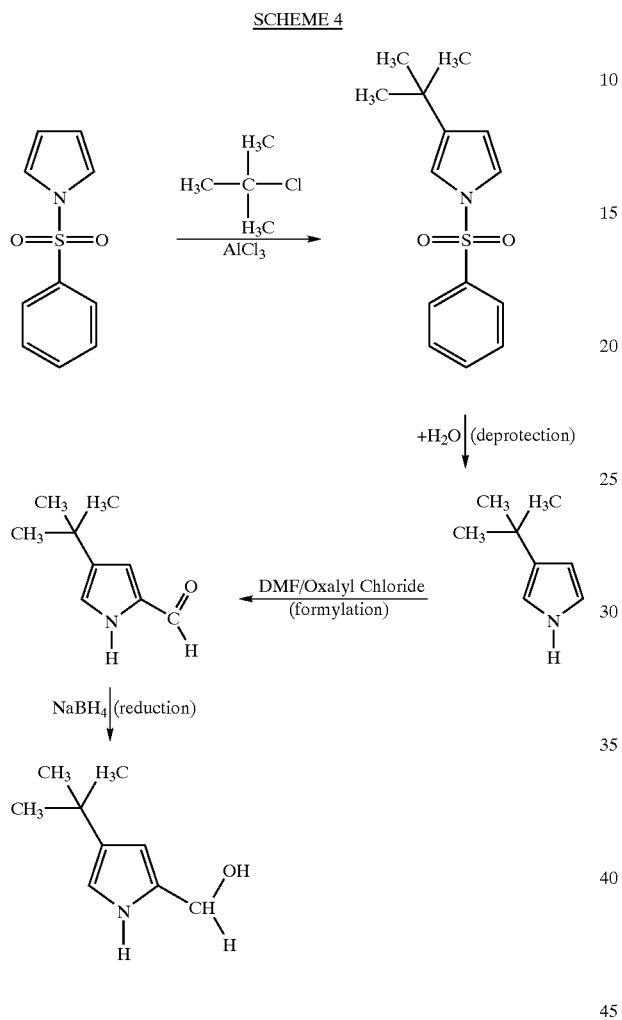

Compounds of formulas I or VI may also be prepared by a modification of the method of Scheme 4. For example, the 4-t-butyl pyrrole-2-carbaldehyde of Scheme 4 can be prepared by alkylation of pyrrole-2-carbaldehyde using t-butylchloride in the presence of aluminum chloride, as disclosed in U.S. Provisional Patent Application No. 60/160,776, filed Oct. 21, 1999, which is hereby incorporated by reference in its entirely, for the purpose of its teachings of improved methods of preparing 4-alkyl-substituted pyrrole-2-carbaldehydes. The 4-alkyl-substituted pyrrole-2-carbaldehydes may be further reduced to compounds of formulas I or VI, by methods which include those shown in Scheme 4.

Although the foregoing reaction scheme stops with the reduction step forming the hydroxy leaving group, should other leaving groups be desired, the hydroxy substituent can be effectively reacted to form the leaving group in question. Preferred reaction conditions for producing the substituted pyrrole are dependent on the particular steps performed and as such are recognized in the art in connection with the particular synthesis step.

Examples of suitable reaction conditions which can effect the efficiency of the reaction include time, temperature, the presence or absence as well as level of catalyst, the techniques for isolating products, and the like.

The present invention also relates to both porphyrin compounds and pyrrole intermediates useful in forming the porphyrin compounds.

Examples of porphyrin compounds include those of Formulae (II) and (V) with examples of pyrrole compounds are those of Formulae (I), (VI) and (VII).

Formula II

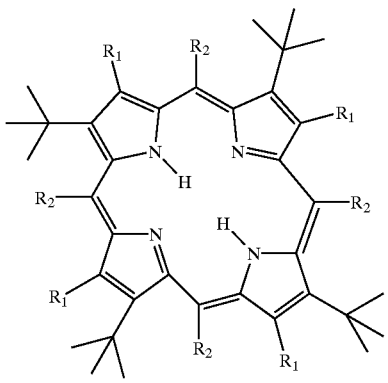

Formula V

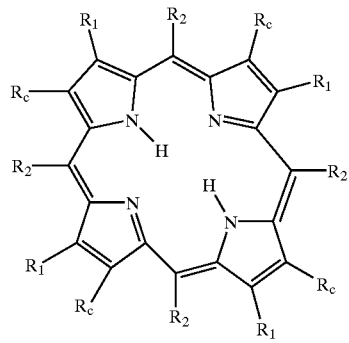

Formula I

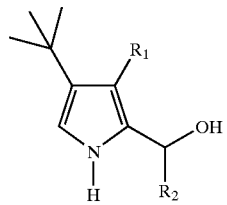

Formula VI

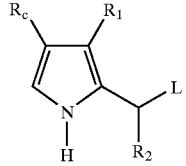

Formula VII

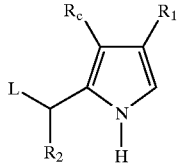

In the foregoing formulae, $R^1$ and $R^2$ can be any substituent desired for use in connection with porphyrin compound. Examples of such substituents include hydrogen, aryl, alkyl, halogens, and the like.

Moreover, in those instances where it is desired that the porphyrin compound be a metallated porphyrin compound, a metal salt can be optionally included in one of the foregoing steps. For example, the condensation step used in porphyrin ring formation can be effectively performed in the presence of an optional metal salt in order to provide a metallated porphyrin. Examples of suitable metals include Mg, Fe, Zn, Ni and transition metals.

The inventive method is capable of providing a number of significant advantages, not the least of which is a better yield at a lower cost. For example, the substituted porphyrin can be made in very high yield (70–80%) using a substituted pyrrole. The substituent can aid in the porphyrin ring formation allowing 50-fold more concentrated reaction conditions. Due to its superior solubility, purification of this porphyrin can be provided much easier as compared to porphine. For example, porphine can then be formed in 70–80% yield by removal of the substituent(s); no further chromatography is required. Specifically, this invention can generate 20 g–40 g (or more) of porphine in a 5 L vessel, whereas correct state of the art technology can make only 200 mg in the same size reaction vessel. This strategy can also allow a general synthesis of beta-and meso-substituted porphyrins, generating higher yields of products at much higher concentrations.

This invention may, however, be embodied in many different forms and should not be construed as limited to the embodiments set forth herein; rather, these embodiments are provided so that this disclosure will be thorough and complete, and will fully convey the scope of the invention to those skilled in the art.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

For example, as discussed above, the aldehyde can be reduced to the alcohol using sodium borohydride and isolated by ether extraction and drying with $MgSO_4$. This produced a material that is unstable and needs to be used immediately. The alcohol is then added drop-wise over 5 minutes to the solvent and the acid (20 mol %), which, after DDQ oxidation and purification provides TTBP in 80–82% yield. However, the yields of the intended isomer I (of four possible isomers) range from 45–55%.

Alternatively, a procedure which does not dry the alcohol can be employed. The "wet" alcohol is more stable than the dried form and is thus easier to handle. The order of addition can also be reversed. The acid (10 mol %) can be added to the alcohol dissolved in a chlorinated solvent (dichloroethane here) containing 10–15% acetic anhydride. The reaction can be complete within 5 minutes. After DDQ oxidation and purification (isolation is the same as previously disclosed) the product porphyrin TTBP is obtained in 60–70% yield with an isomer I content of 65–75%.

An example of a typical procedure using acetic anhydride:

t-Butylpyrrole-2-carboxaldehyde (16.0 g, 106 mmol) is reduced with $NaBH_4$ (1.33 g, 0.035 mol) in methanol and water. The product alcohol is isolated by hexanes extraction and washed once with brine. The solvent is removed by rotary evaporation. Dicholorethane (140 mL) and acetic anhydride (1 mL, 10.6 mmol) are added, and the reaction vessel is then protected from light and placed in a RT water bath. Trifluoroacetic acid (816 $\mu$L 10.6 mmol) is then added via syringe. After 15 minutes, DDQ (8.6 g, 80 mmol) is added and the mixture stirred for 30 minutes. Excess triethylamine is then added to neutralize the acid and reduced DDQ. The product porphyrin (as a mixture of isomers) is then isolated by filtration through silica using dichloroethane as eluent.

What is claimed is:

1. A method for making porphyrin compounds comprising:

(a) providing a substituted porphyrin compound including one or more hydrocarbyl substituent groups having a tertiary carbon, wherein the hydrocarbyl substituent groups are bonded to the porphyrin ring and are capable of being removed; and (b) removing the hydrocarbyl substituent groups to provide a porphyrin compound.

2. The method according to claim 1 wherein step (b) involves acid cleaving of the substituent group with a Bronstead acid.

3. The method according to claim 1 wherein the hydrocarbyl substituent group is an acid cleavable alkyl group.

4. The method according to claim 1 wherein the hydrocarbyl substituent group is a t-butyl group.

5. A method for making porphyrin compounds comprising:

(a) providing a substituted pyrrole compound, said pyrrole compound including a hydrocarbyl substituent group having tertiary carbons;

(b) reacting the hydrocarbyl substituted pyrrole compound to obtain a substituted porphryin containing one or more of the hydrocarbyl substituent groups located on the porphyrin ring;

(c) removing the hydrocarbyl substituent groups from the substituted porphyrin compound.

6. The method according to claim 5 wherein step (b) comprises a condensation step.

7. The method according to claim 6 wherein the condensation is performed in the presence of a Bronstead acid, and an optional metal salt.

8. The method according to claim 5 wherein, step (c) involves the acid cleavage of the hydrocarbyl substituent group.

9. The method according to claim 5 wherein, the hydrocarbyl substituent group is a t-butyl group and step (c) involves de t-butylation.

10. The method according to claim 5 wherein the substituted pyrrole compound further includes at least one leaving group bonded to the carbon of an R—CH— substituent bonded to the 2-position of the pyrrole ring, wherein R is H, hydrocarbyl, or substituted hydrocarbyl.

11. The method according to claim 10 wherein, the leaving group is a hydroxy group.

12. The method according to claim 5, wherein the hydrocarbyl substituent is a t-butyl group.

13. A method of forming a porphyrin compound according to the following reaction scheme 1

SCHEME I

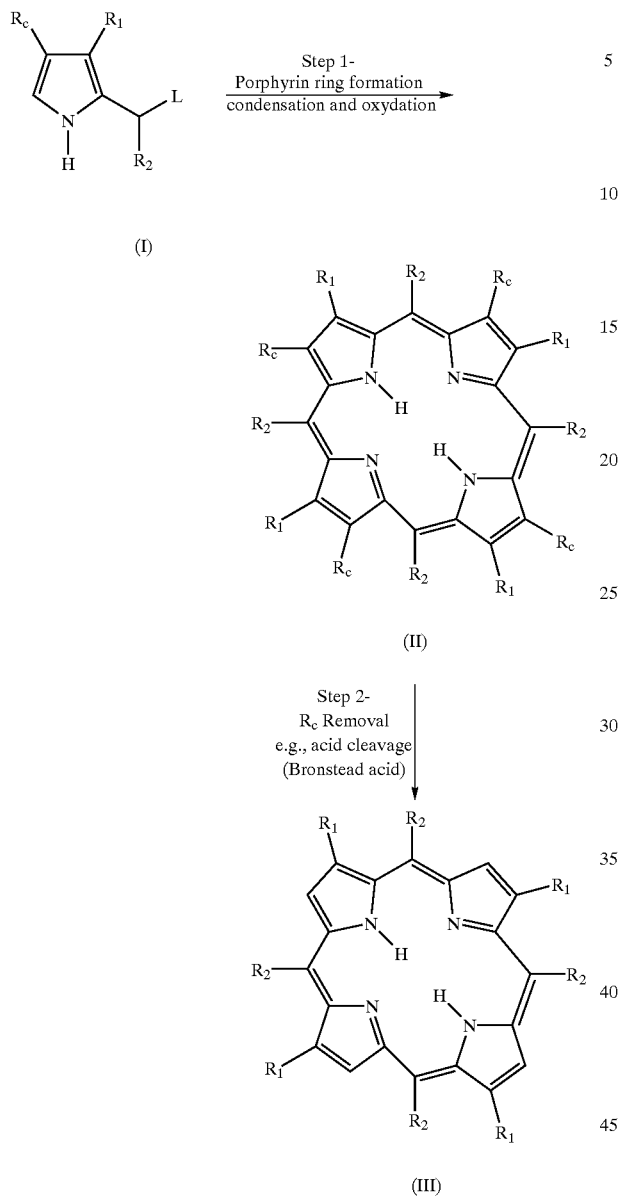

wherein $R_c$ is a hydrocarbyl substituent groups with tertiary carbons, $R_1$ and $R_2$ are independently H, alkyl, aryl or a halogen, and wherein at least one of $R_1$ or $R_2$ is not H on formulas II or III, and L is a hydroxy group, a carboxylate, a benzoate, a phosphate, a sulfonate, a sulfone, a carbonyl, or nitrogen based leaving group.

14. A method of forming a porphyrin compound according to the following reaction scheme 2

SCHEME 2

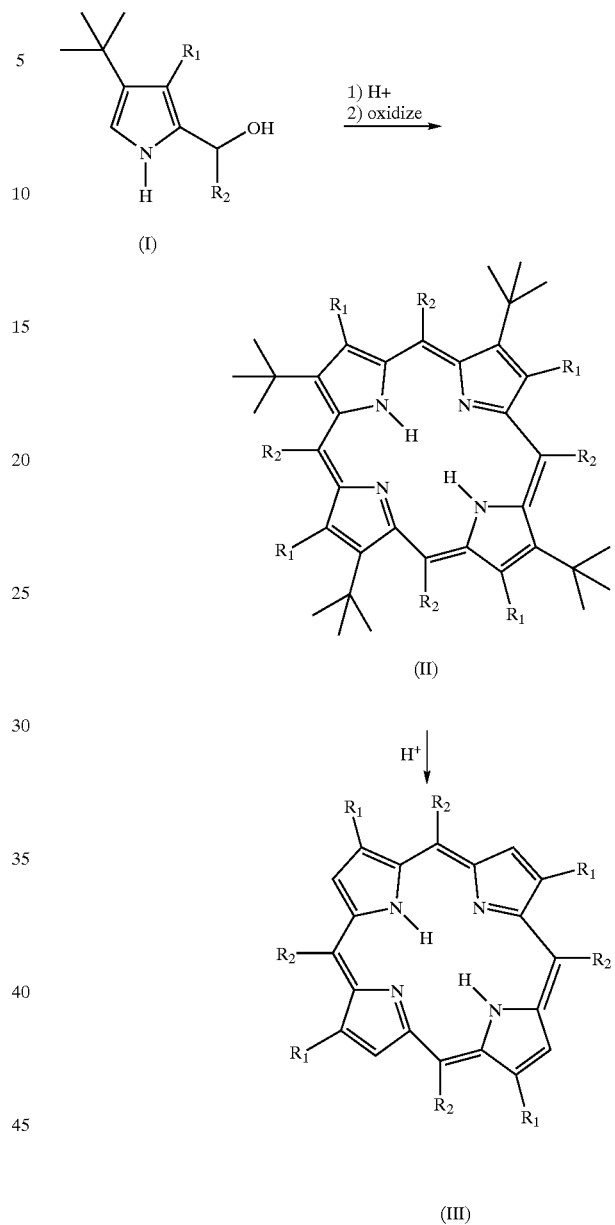

$R_1$ = H, alkyl, aryl, or X
$R_2$ = H, alkyl, aryl, or X wherein, $R_1$ and $R_2$ are independently H, alkyl, aryl or a halogen, and wherein at least one of $R_1$ or $R_2$ is not H on formulas II or III.

* * * * *